(12) United States Patent
Gilson et al.

(10) Patent No.: US 6,669,716 B1
(45) Date of Patent: Dec. 30, 2003

(54) DELIVERY CATHETER

(75) Inventors: Paul Gilson, County Galway (IE); Gary S. Roubin, New York, NY (US)

(73) Assignee: Salviac Limited, Dublin (IE)

( * ) Notice: Subject to any disclaimer, the term of this patent is extended or adjusted under 35 U.S.C. 154(b) by 21 days.

(21) Appl. No.: 09/672,014

(22) Filed: Sep. 29, 2000

Related U.S. Application Data

(63) Continuation of application No. PCT/IE99/00018, filed on Mar. 31, 1999.

(30) Foreign Application Priority Data

Mar. 31, 1998 (IE) .................................................. 980235

(51) Int. Cl.⁷ .......................... A61B 17/00; A61M 29/00
(52) U.S. Cl. ...................... 623/1.11; 606/108; 606/198
(58) Field of Search ............................... 623/1.11–1.2; 606/191, 194, 195, 198, 192, 200, 108; 604/96

(56) References Cited

U.S. PATENT DOCUMENTS

| | | | | |
|---|---|---|---|---|
| 5,433,723 A | | 7/1995 | Lindenberg et al. | |
| 5,534,007 A | * | 7/1996 | St. Germain et al. | 623/1.11 |
| 5,827,322 A | * | 10/1998 | Williams | 623/1.18 |
| 5,906,619 A | * | 5/1999 | Olson et al. | 606/108 |
| 6,077,295 A | * | 6/2000 | Limon et al. | 623/1.11 |

FOREIGN PATENT DOCUMENTS

| | | |
|---|---|---|
| EP | 0 536 610 | 4/1993 |
| EP | 0 819 411 | 1/1998 |

* cited by examiner

*Primary Examiner*—Vy Q. Bui
(74) *Attorney, Agent, or Firm*—Finnegan, Henderson, Farabow, Garrett & Dunner, LLP

(57) ABSTRACT

A rapid exchange stent delivery catheter for delivery and deployment of a stent has a catheter shaft having a guidewire lumen defined by a passageway with an entrance and an exit. The stent is of a shape memory metallic alloy and is constrained by a sheath. The sheath has an elongate slot aligned with the guidewire lumen entrance so that a guidewire is not obstructed during movement of the sheath to deploy the stent. The sheath is pulled back linearly by a thumbscrew mechanism to deploy the stent.

11 Claims, 12 Drawing Sheets

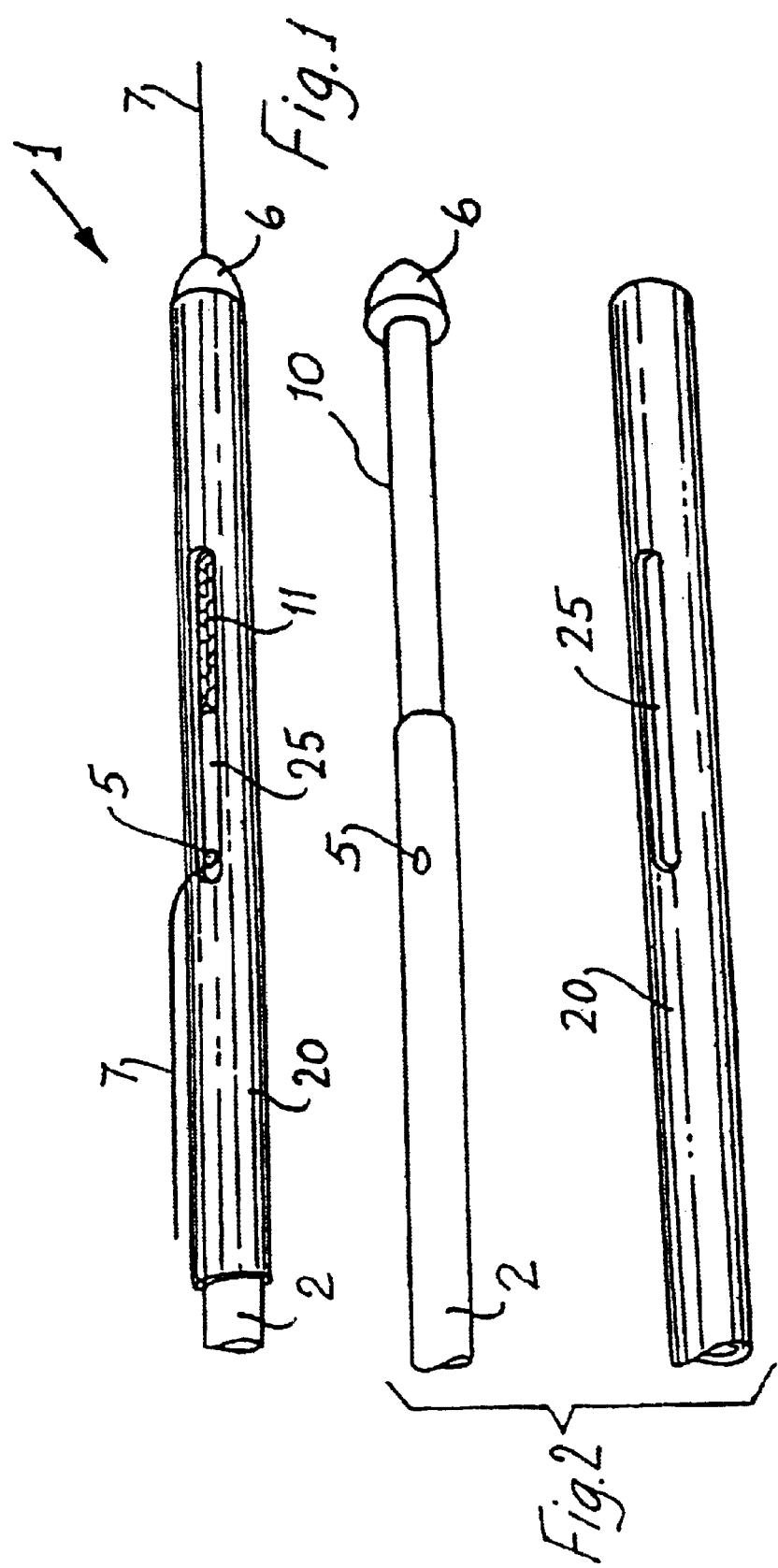

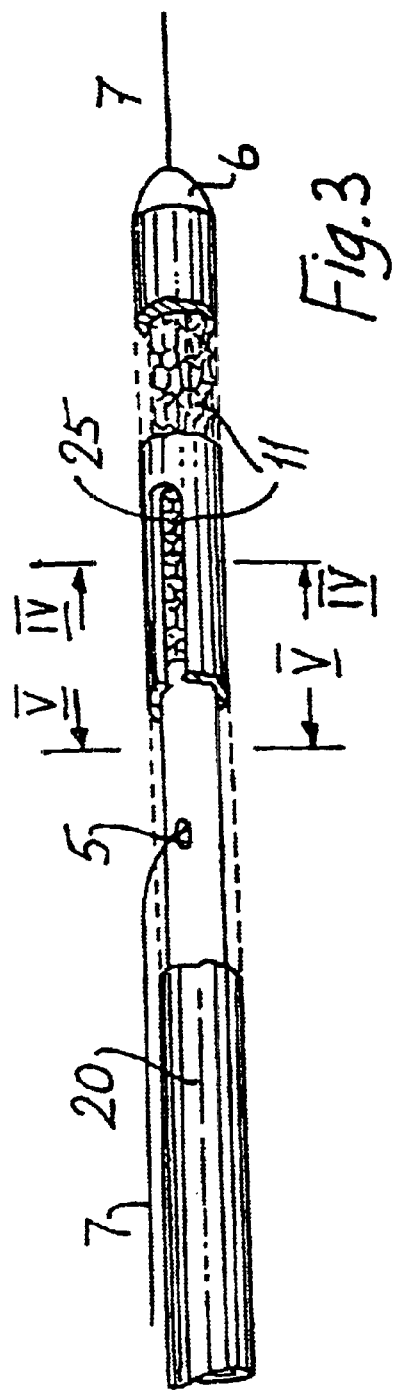
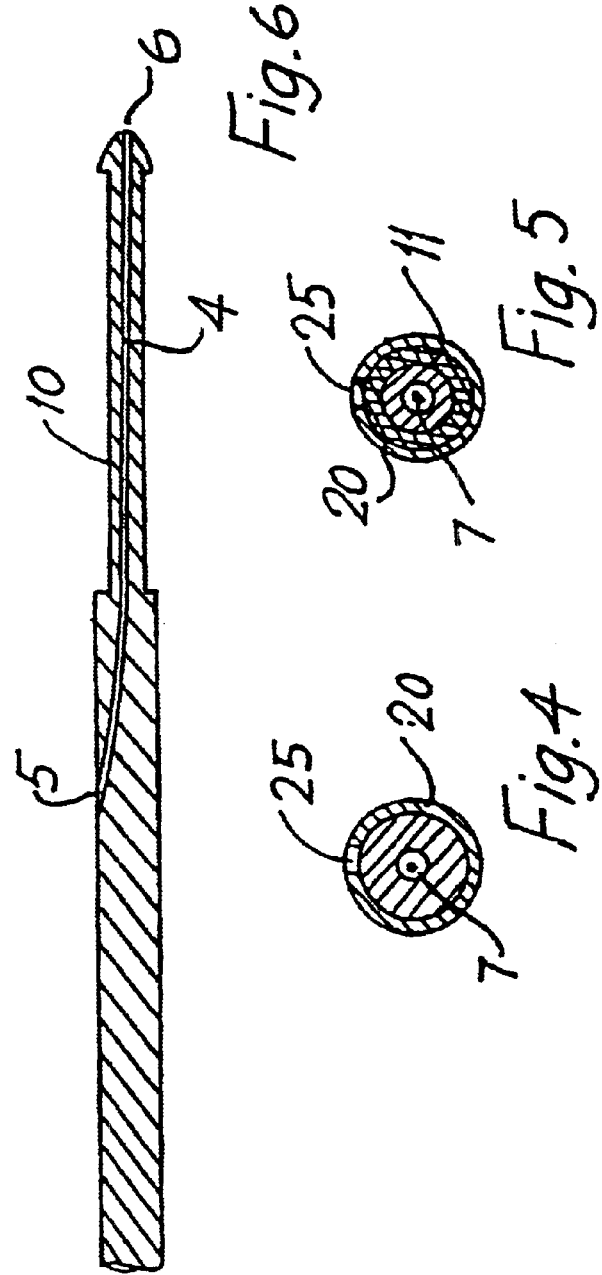

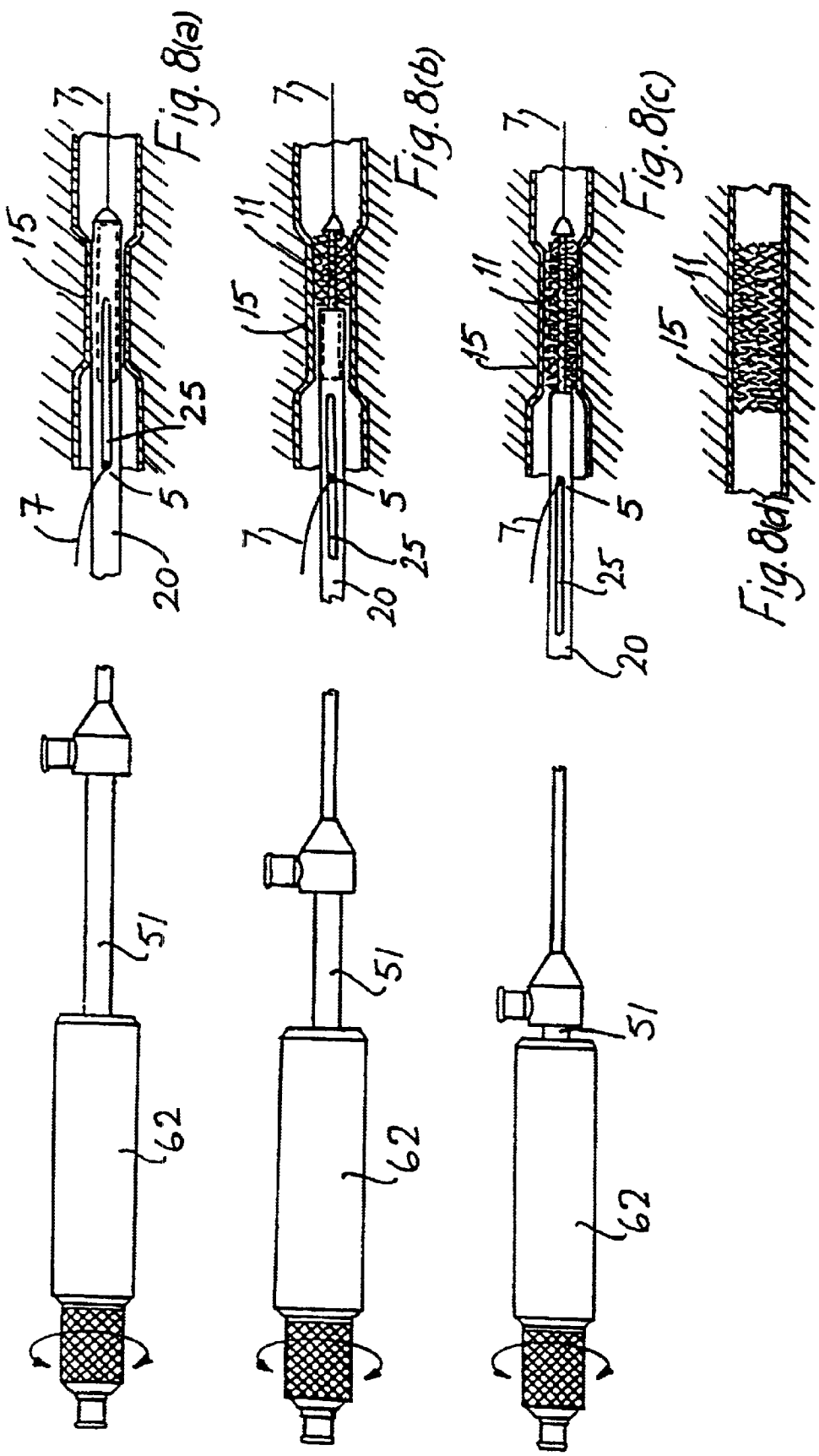

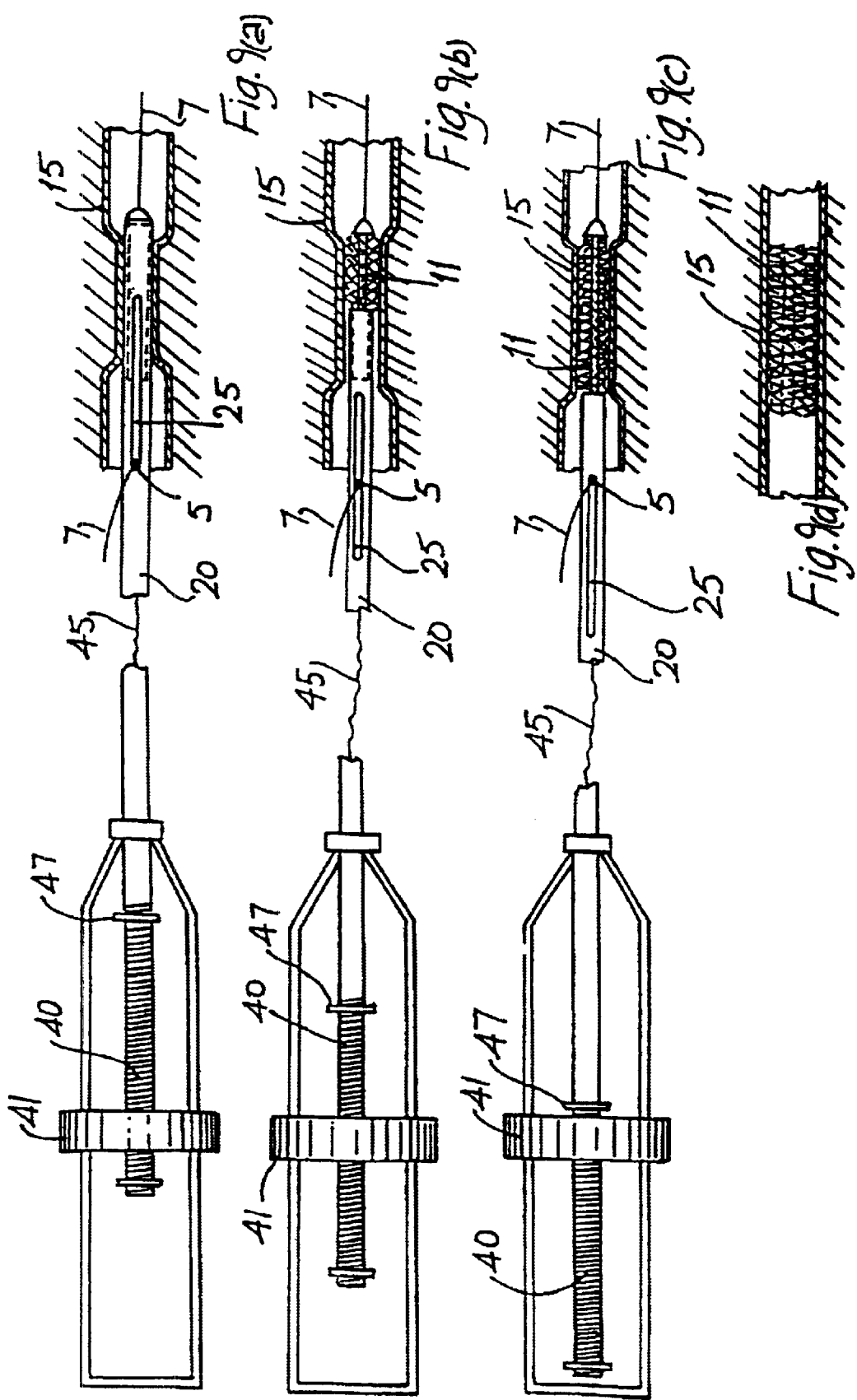

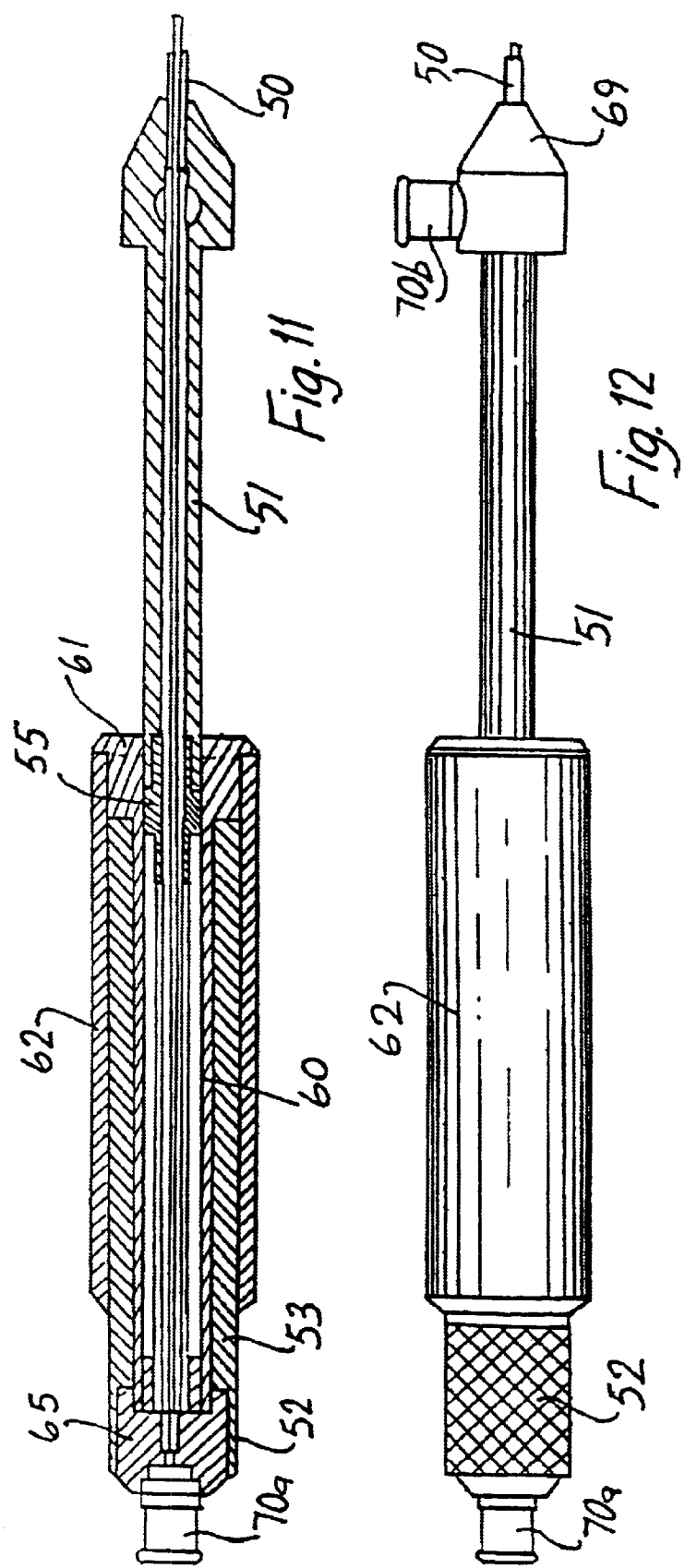

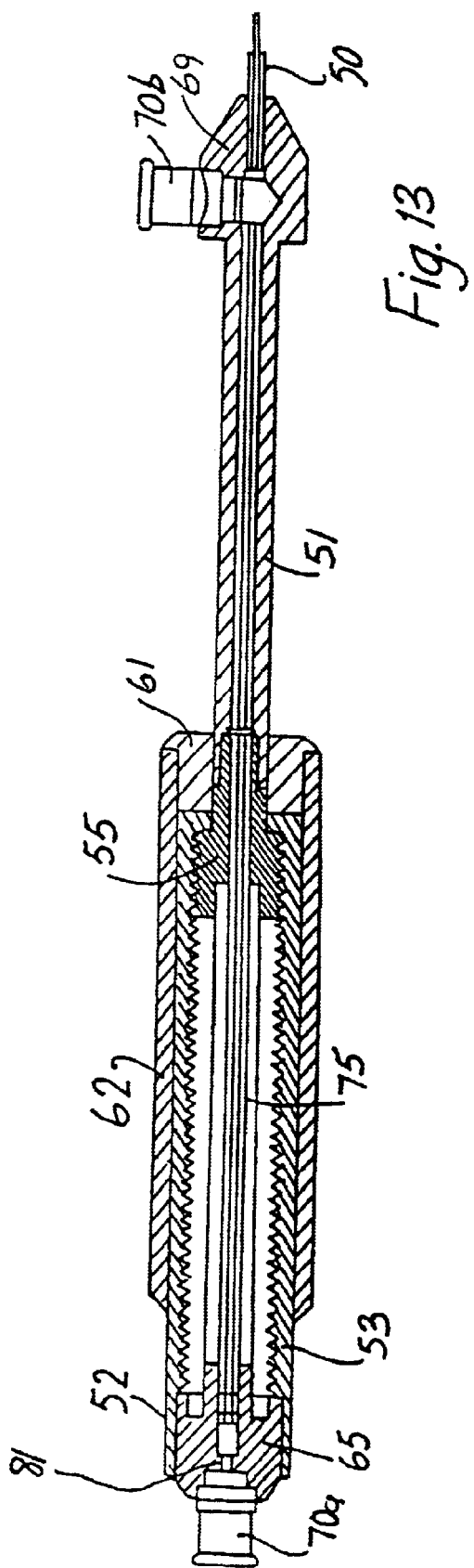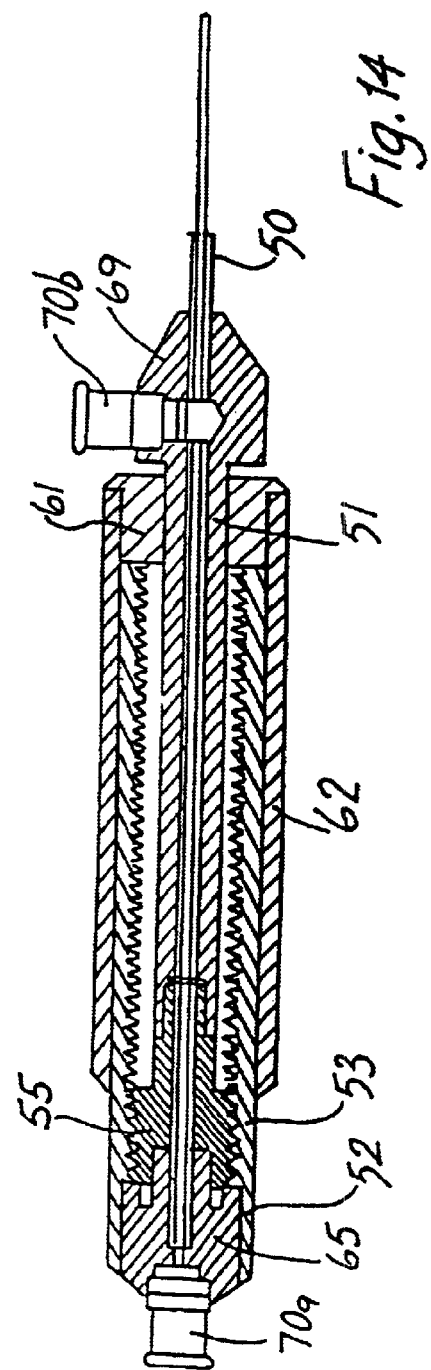

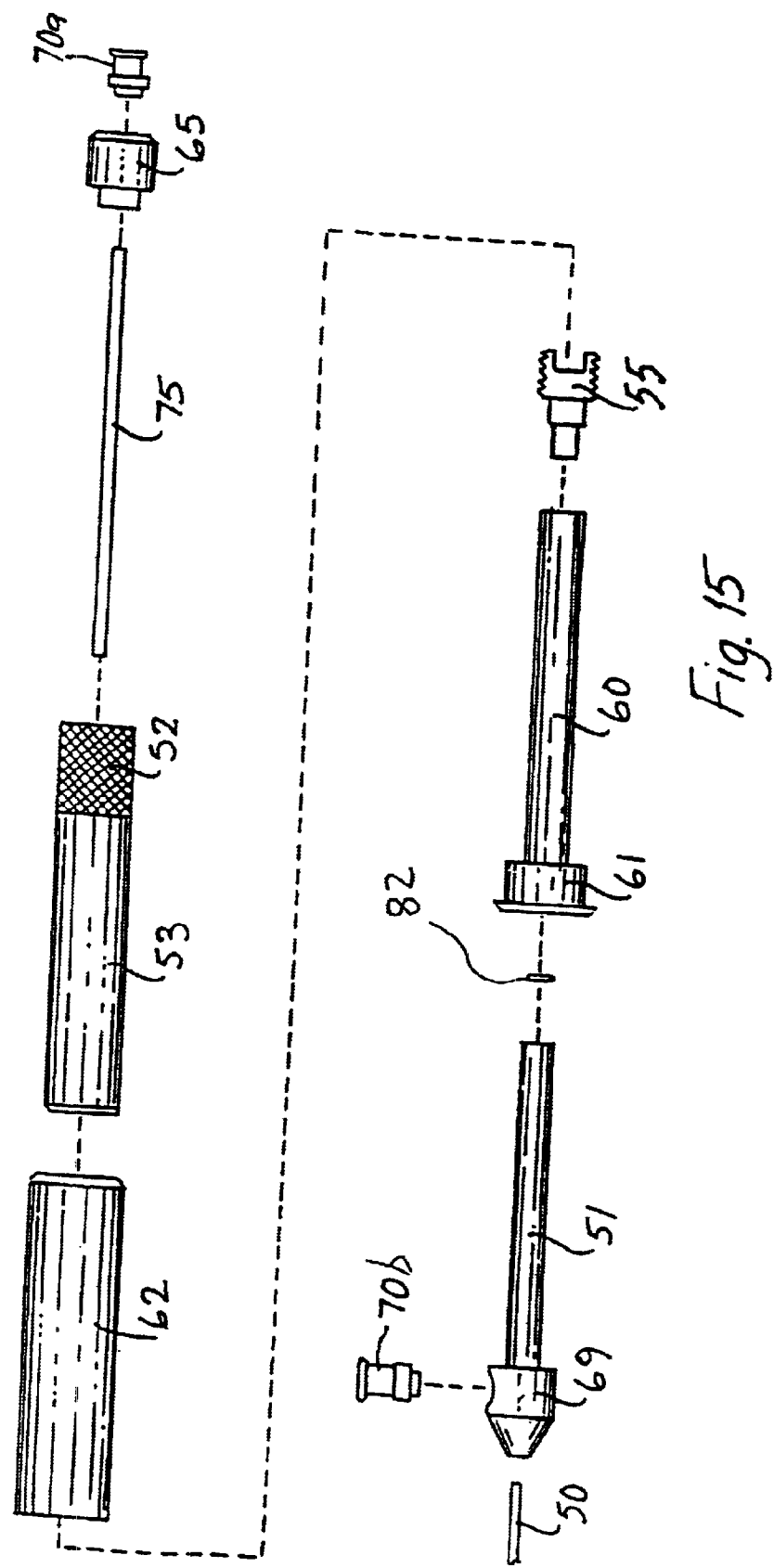

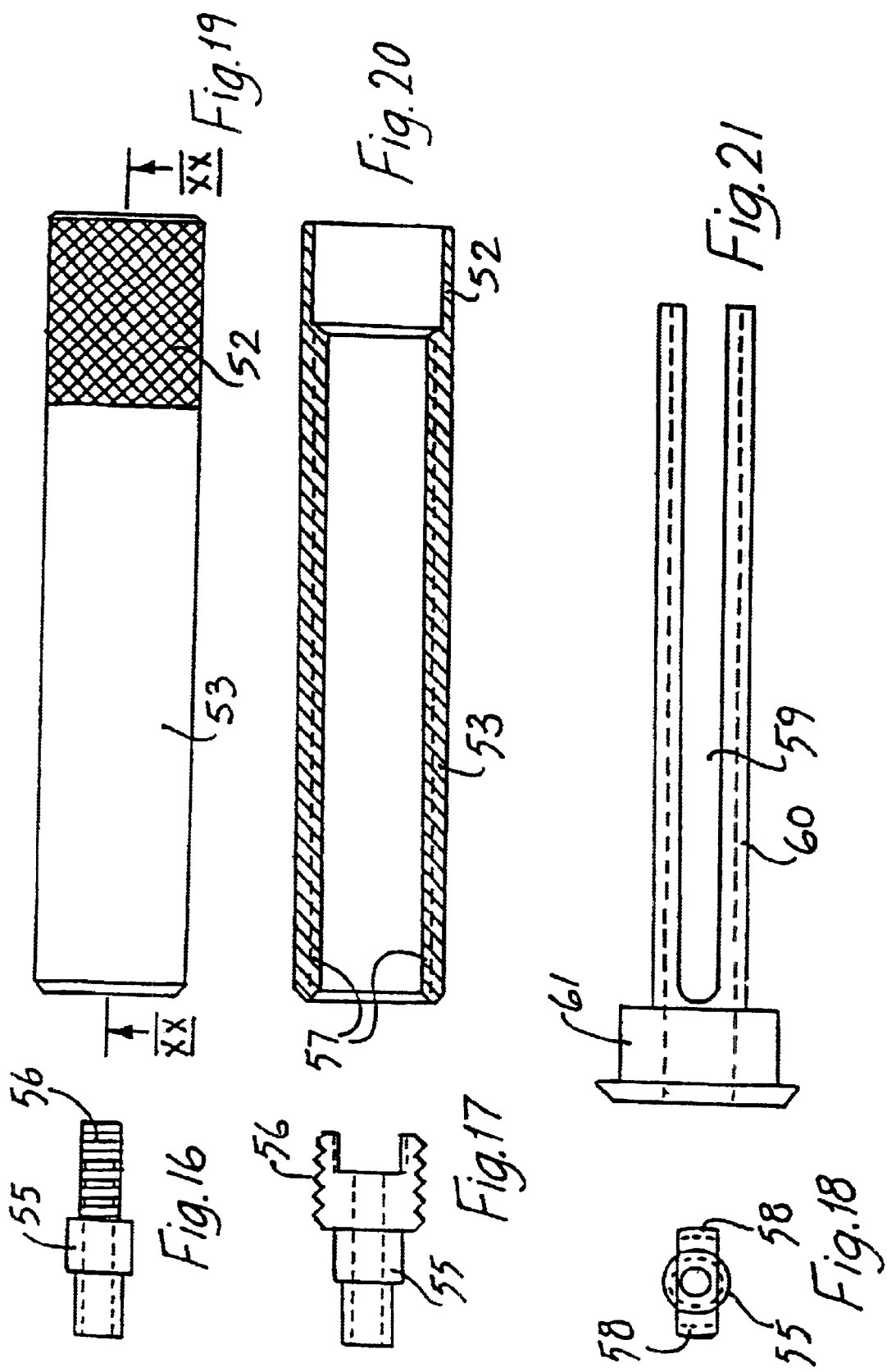

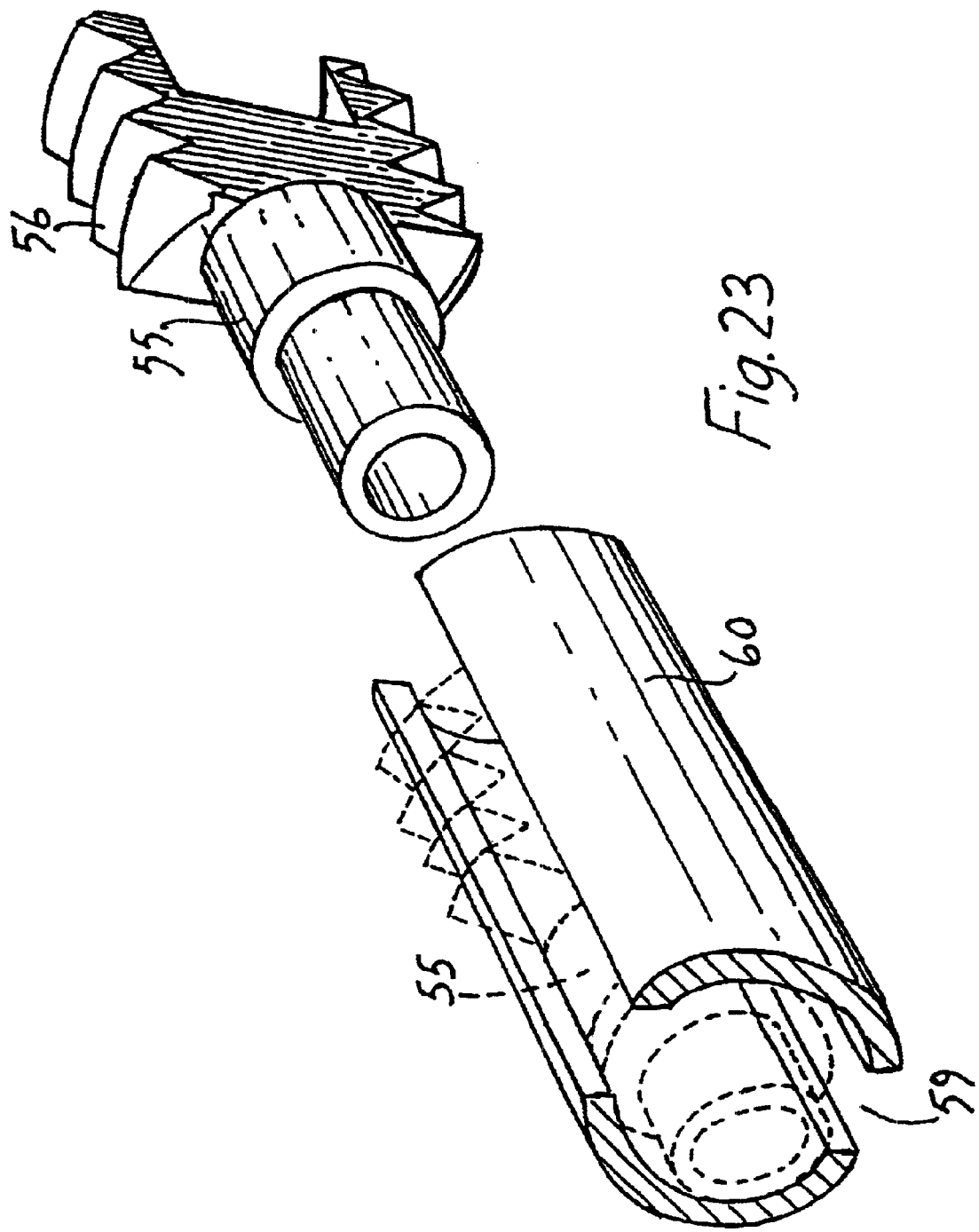

DELIVERY CATHETER

This is a continuation of PCT Application No. PCT/IE99/00018, filed Mar. 31, 1999.

The invention relates to a delivery system for delivery and deployment of a stent, to a desired vascular location.

Vascular intervention is today undertaken to treat a large number of diseases that had heretofore been treated by surgery. Stents are used widely in a number of applications to provide structural support to vessels that are being treated. Typically, a vascular intervention procedure is required to restore the flow of blood through an artery that has been constricted by a build up of atherosclerotic material. Medical practice has shown that implanting stents at the site of disease is effective. Various types of stents have been devised and the therapy is well known and widely practised.

Stent designs are broadly divided into two categories, balloon expandable stents and self-expanding stents. The invention relates particularly to the delivery and positioning of self-expanding stents. The term self-expanding refers to the inherent material properties of the stent which cause the expansion of the stent once an external constraint has been removed. The effect is most commonly achieved by using a shape memory metallic alloy such as nitinol.

Generally, stents are delivered to the desired location by means of a catheter, specifically referred to as a delivery catheter. Delivery catheters are threaded through a guiding catheter to the site of the disease and once the correct position has been established by means of fluoroscopic or other imaging method, the stent is deployed.

There is however a problem with conventional stent delivery systems in that it is difficult and time consuming to deploy stents. A full length over the wire catheter is used in combination with an exchange length guidewire over which the delivery catheter is manipulated. Such systems are cumbersome to handle and a second operator is generally required to assist the lead clinician in controlling the procedure. When the guidewire is positioned at the commencement of the procedure, it is desirable that it's position is stable during the remainder of the procedure as it provides access to the treatment site for the therapeutic or diagnostic devices used in treatment. If it is desirous to insert or exchange a catheter, it is necessary to thread the catheter over the guidewire while retaining control of the guidewire. This is achievable only if the length of available guidewire outside the body is greater than the length of the catheter being loaded. Intravascular catheters typically measure 1.3 metres or more. It is impossible for one clinician to maintain position and control of a guidewire and simultaneously thread on a catheter more than a metre away.

There is therefore a need for a delivery catheter system which will overcome at least some of these difficulties.

STATEMENTS OF INVENTION

According to the invention there is provided a stent delivery catheter for delivery and deployment of a stent comprising:
an elongate catheter body;
a self-expanding stent overlying said catheter body at a distal end thereof;
a sheath overlying said stent to constrict the stent during delivery;
the catheter body having a guidewire lumen with a guidewire exit at a distal end of the catheter body and a guidewire entrance proximal of the stent;
a guidewire extending through the lumen between the guidewire entrance and the guidewire exit; and
stent deployment means comprising means for moving the sheath relative to the catheter body to release the stent;
the sheath having guidewire accommodating means for accommodating the guidewire so that the guidewire entrance is not obstructed during movement of the sheath relative to the catheter body.

Most preferably the guidewire accommodating means is an opening in the sheath which is arranged to align with the guidewire entrance to prevent obstruction of the entrance on deployment of the stent.

Preferably the guidewire accommodating means is configured to correspond with the operation of the stent deployment means.

In a preferred arrangement the sheath opening has a length which is greater than or equal to the length of the stent to be deployed.

Ideally the sheath opening comprises an elongate slot.

Preferably the stent deployment means is a linear actuating means. In a preferred arrangement the actuating means includes converter means for converting rotational movement of an actuator into linear motion to move the sheath linearly.

Preferably the converter means comprises a shuttle which is linearly movable within a shuttle guide, on rotation of the actuator.

Ideally the shuttle screw threadingly engages the actuator. Preferably the thread has at least two starts. Ideally, the thread is a four start thread.

In one embodiment of the invention the actuator is a shuttle nut. Preferably the shuttle nut includes an operator handle. The operator handle may be a knurled portion of the shuttle nut.

In a particularly preferred arrangement the shuttle has at least two wings and the guide includes corresponding slots to substantially prevent rotation of the wings on rotation of the actuator. The oppositely directed wings have the effect of stabilising the shuttle in the guide slots.

A shuttle shaft preferably is connected to and extends forwardly of the shuttle. The shuttle shaft thereby provides an extension of the shuttle. Preferably the sheath is attached to the shuttle shaft.

The actuating means may comprise a threaded shaft and an associated thumbwheel which is rotated to move the shaft linearly. An anti-rotation means to control rotation of the threaded shaft is preferably provided. The thread on the shaft may be discontinuous. Ideally the thread is a multistart thread, preferably a four start thread.

In another arrangement the restraining sheath is slit helically at one or more circumferential location such that a combined linear and rotational motion of the sheath will maintain the opening for the guidewire to pass freely.

Preferably the stent deployment means is attached to the sheath. Typically, the actuating means includes a pull wire attached directly or indirectly to the sheath.

The invention also provides a constriction sheath for use with a delivery catheter of the invention. The constriction sheath has an opening which may be arranged to align with the guidewire lumen entrance to prevent obstruction of the entrance on movement of the constriction sheath.

In a particularly preferred arrangement the opening is an elongate slot having a length which is greater than or equal to the length of a stent to be deployed.

The invention further provides a catheter for deploying a stent, the catheter having a pathway extending longitudinally and in parallel with a coaxial guidewire to permit free movement of the guidewire and providing a path for a stent release means.

Thus, the invention provides a means for rapidly deploying a self-expanding stent by way of a pull or push motion of the sheath without interference with any guidewire path.

The invention also provides a restraining sheath that is slit longitudinally at one or more circumferential location such that linear motion of the sheath will maintain the opening for the guidewire to pass freely.

The invention further provides a restraining sheath that is slit helically at one or more circumfrential location such that a combined linear and rotational motion of the sheath will maintain the opening for the guidewire to pass freely.

The invention further provides a rapid exchange stent delivery catheter having a pathway extending longitudinally and in parallel with a coaxial guidewire to permit movement of the guidewire and providing a path for a pull wire or suture used to release a stent restraining sheath.

BRIEF DESCRIPTION OF THE DRAWINGS

The invention will be more clearly understood from the following description thereof given by way of example only in which:

FIG. 1 is a perspective, partially cut-away view of part of a rapid exchange stent delivery catheter according to the invention;

FIG. 2 is an exploded view of the delivery catheter of FIG. 1;

FIG. 3 is a perspective, partially cut-away view of the delivery catheter;

FIG. 4 is a cross sectional view on the line IV—IV in FIG. 3;

FIG. 5 is a cross sectional view on the line V—V in FIG. 3.

FIG. 6 is a side cross sectional view of part of the catheter of FIGS. 1 to 5;

FIGS. 8(a) to 8(d) are views similar to FIGS. 7(a) to 7(d) with one stent deployment actuating mechanism;

FIGS. 9(a) to 9(d) are views similar to FIGS. 7(a) to 7(d) with another stent deployment actuating mechanism;

FIG. 11 is a plan cross sectional view of the actuating mechanism of FIG. 10;

FIG. 12 is a side elevational view of the actuating mechanism of FIG. 10;

FIGS. 13 and 14 are side cross sectional views of the actuating mechanism of FIG. 10 in different positions of use;

FIG. 15 is an exploded side view of a stent deployment system incorporating the actuating mechanism of FIG. 10;

FIG. 16 is a plan view of a shuttle forming part of the actuating mechanism of FIG. 10;

FIG. 17 is a side elevational view of the shuttle of FIG. 16;

FIG. 18 is an end view of the shuttle FIGS. 16 and 17;

FIG. 19 is a side elevational view of a shuttle nut forming part of the actuating mechanism of FIG. 10;

FIG. 20 is a cross sectional view on the line XX—XX in FIG. 19;

FIG. 21 is a plan view of a guide forming part of the actuating mechanism of FIG. 10;

FIG. 23 is a diagrammatic exploded perspective view of another part of the actuating mechanism of FIG. 22.

DETAILED DESCRIPTION

Figure 7A:
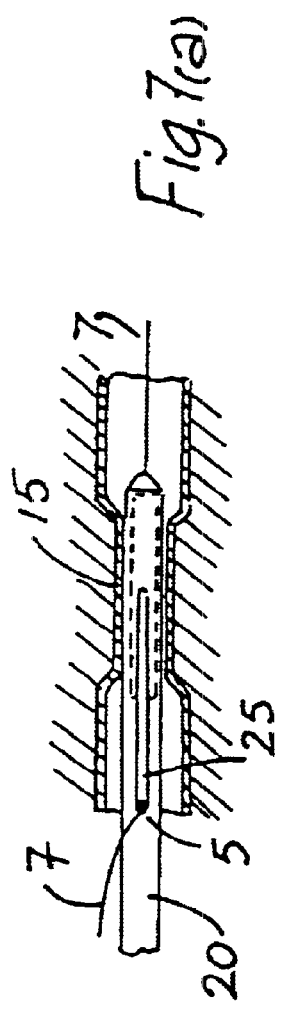
FIGS. 7(a) to 7(d) are diagrammatic views illustrating the delivery catheter of FIGS. 1 to 6, in use.
Figure 7B:
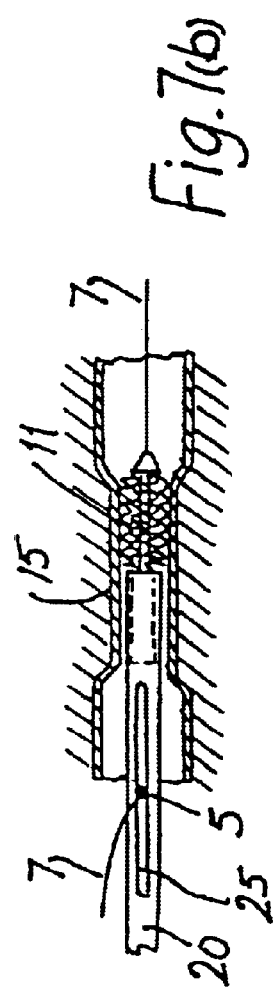
Figure 7C:
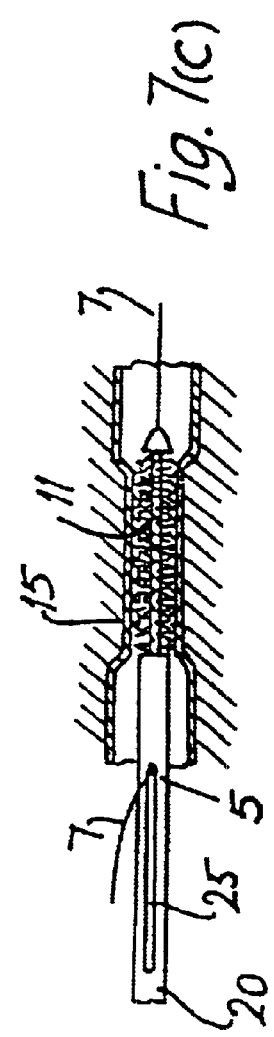
Figure 7D:
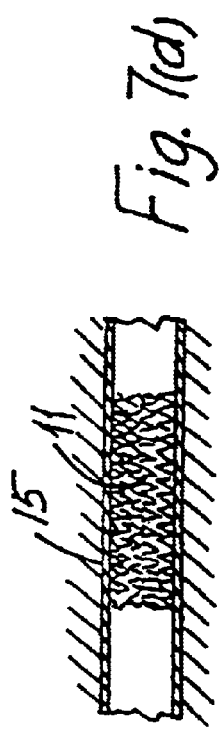
Figure 10:
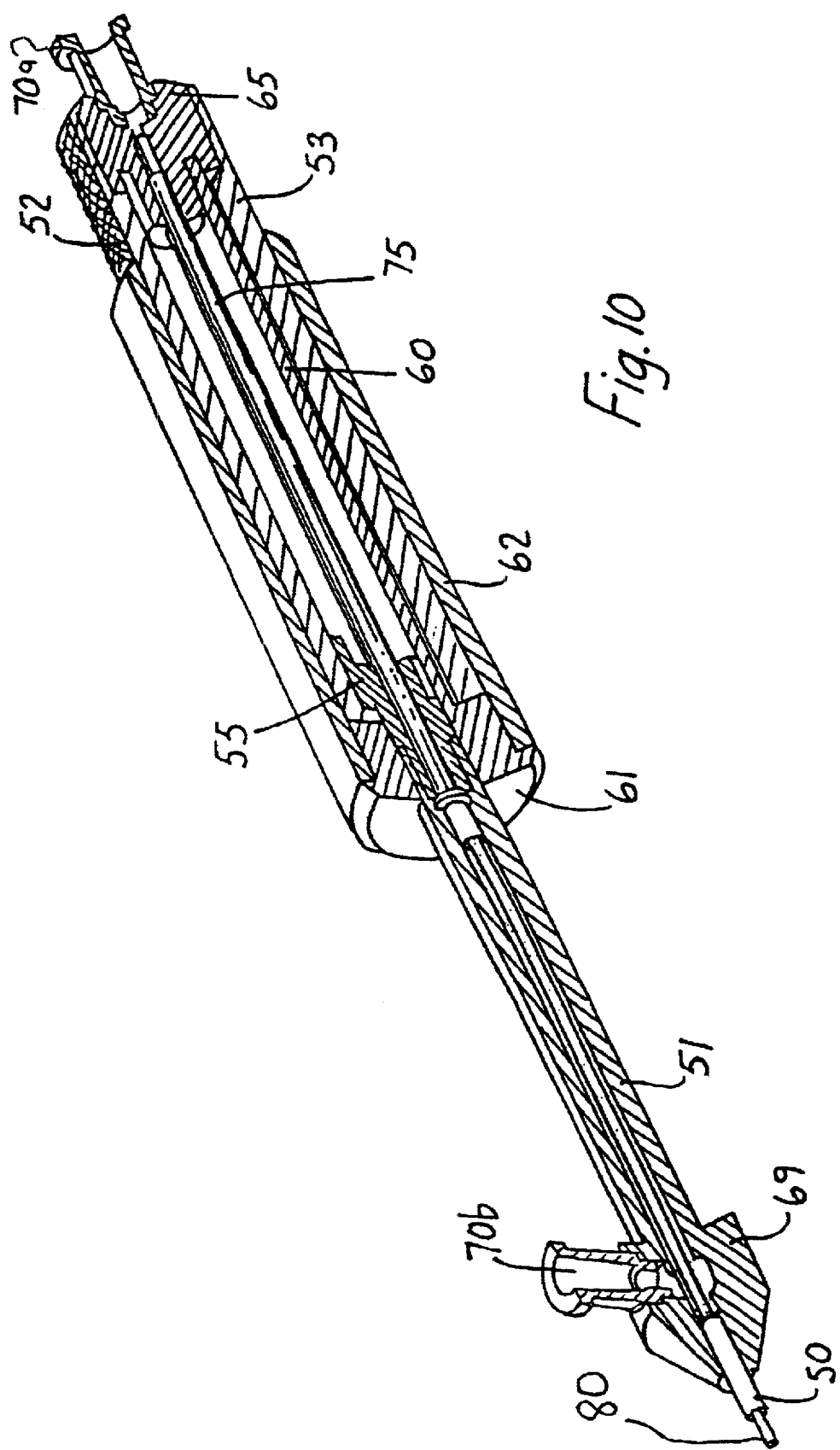
FIG. 10 is a perspective, partially cut-away cross sectional view of the stent deployment actuating mechanism of FIG. 8.

Referring to the drawings there is illustrated a rapid exchange stent delivery catheter 1 having a catheter shaft 2 defining a bore and a guidewire lumen 4 defined by a passageway having an entrance 5 and an exit 6. A guidewire 7 extends through the lumen 4. Around the lumen 4 a stepped recess 10 is provided for receiving a stent 11. The stent 11 is of a shape memory metallic alloy such as nitinol and is constrained in a pre-use constrained position by a sheath 20. The sheath 20 prevents the stent 11 from-expanding until a desired location has been reached. By loading the distal end of the lumen over a guidewire 7 it is possible to advance the catheter to any desired position. The sheath 20 is then moved linearly by means of a stent deployment means to remove the constraint on the stent 11 and thereby allow it to be deployed by expanding into contact with a vessel wall 15 as illustrated in FIGS. 7 to 9.

The sheath 20 is movable to deploy the stent 11 without obstructing the guidewire lumen entrance 5. An opening, in this case in the form of an elongate slot 25 is provided in the sheath 20 to align with the guidewire lumen entrance 5 so that the guidewire 7 is not obstructed during movement of the sheath 20 to deploy the stent 11. The slot 25 has a length which is greater than or equal to the length of the stent 11 to be deployed and a width which is at least the same size as, and preferably larger than, the guidewire 7 so that, on linear movement of the sheath 20, the guidewire entrance 5 is not interfered with.

Actuating means for moving the sheath 20 to deploy the stent 11 is preferably a linear actuating means. Referring to FIGS. 10 to 14 there is illustrated one such stent deployment/actuating mechanism. The mechanism is used to move a rod or pull wire 50 which is attached directly or indirectly to the sheath 20 by any suitable jointing means. For example, the sheath 20 may have its diameter reduced by way of a constraining shrink tube which may be shrunk onto either the rod 50 or alternatively onto an adhesive layer on the rod 50. Alternatively, a ring bonded to sheath 20 may be attached to the rod 50 by welding, brazing or adhesive.

The rod 50 is fixed to and extends from a shuttle shaft 51 which is movable on rotation of an operator handle defined by a knurled portion 52 of a shuttle nut 53. On rotation of the nut 53 the rod 50 is drawn inwardly from the extended position illustrated in FIGS. 10 to 13 to the retracted position illustrated in FIG. 14.

The shuttle shaft 51 is bonded to a shuttle 55 having a screw threaded portion 56 which screw threadingly engages a corresponding screw threaded portion 57 on the inner surface of the shuttle nut 53. The screw threaded portion 56 of the shuttle 55 is provided on two radially extending wings 58 which are located, on assembly, in corresponding opposed elongated slots 59 defined by elongate arms of a guide 60. The guide 60 has an end-cap forming end 61 which engages, on assembly in an outer body tube 62 of the mechanism. An opposite end of the assembly is closed by an end cap 65 which is a force fit in the barrel of the shuttle nut 53. Female luer connectors 70a, 70b are provided in the end cap 65 and in an elongated head portion 69 of the shuttle shaft 51 respectively.

The rod 50 has an inner core 80 which extends back through the actuating mechanism. The rod 50 which moves the sheath 20 is independently movable of the inner core 80. The rod 50 terminates in the head portion 69 of the shuttle shaft 51. The inner core 80 however continues back through the shuttle shaft 51, the inside of the shuttle 55, an inner tube 75 and is mounted to the rear end cap 65. The end cap 65 has a bore 81 in fluid ccmmunication with the luer connector 70a for flushing the inner core 80. The inner core 80 itself has two lumens and the second luer connector 70b provides a fluid connection for flushing. An O-ring 82 seals the annulus between the inner core 80 and the inner tube 75. Thus, the outer body of the rod 50 is isolated from the inner core 80.

In use, the side wings 58 of the shuttle 55 are trapped in the guide slots 59 of the guide 60 to prevent rotation of the shuttle 55 as the threads 56, 59 engage on rotation of the shuttle nut 53. Thus, the rotational motion of the shuttle nut 53 is converted in to a linear movement of the shuttle 55 which in turn moves the shuttle shaft 51 and the rod 50, to which it is attached, linearly. This is most clearly illustrated in relation to the embodiment of FIGS. 22 and 23

Figure 22:
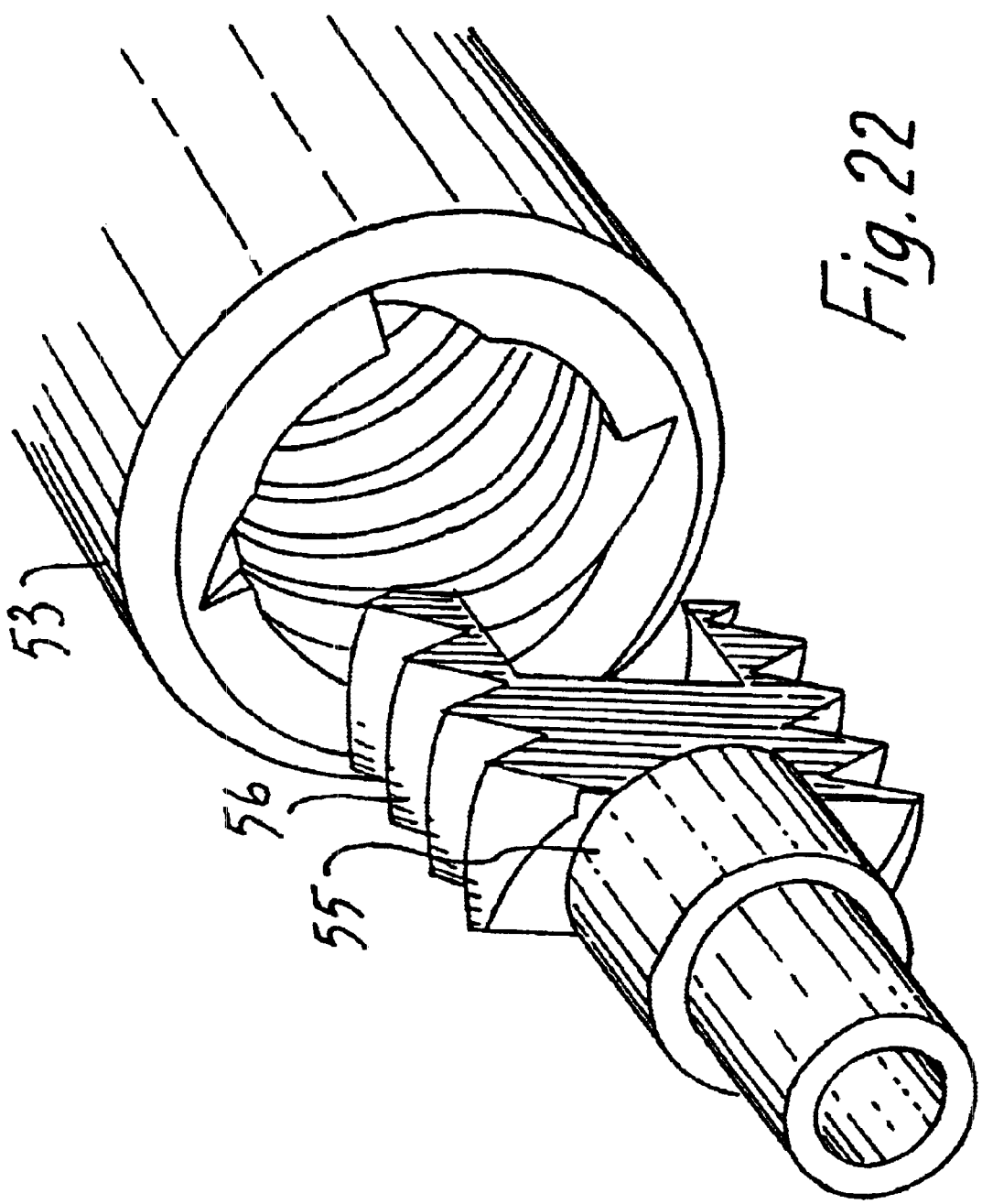
FIG. 22 is a diagrammatic exploded perspective view of one part of another actuating mechanism.

The threading engagement between the threaded wings 58 of the shuttle 55 and the thread 57 inside the shuttle nut 53 provides ease of operation. A multi-start thread is desirable to allow linear actuation in a ratio suitable for the actuation 4 handle in the clinical setting. The ratio of the number of turns to linear travel should be such that a stent of say 10 mm in length should not require excessive rotation. Using a single start thread would require a helix angle that could cause the rotator to bind up. The device is therefore preferably actuated by way of a two start thread as illustrated particularly in FIGS. 17 and 20. Even more desirably the device is actuated by way of a four start thread as illustrated in FIGS. 22 and 23. A thread with a number of starts is preferred as additional points of contact are provided for load sharing.

Referring particularly to FIGS. 9(a) to 9(d) in this example the linear actuating. means comprises a threaded rod 40 rotatably engaged by a thumbwheel 41. The arrangement is such that on rotation of the thumbwheel 41, the rod 40 is moved linearly. An anti rotation pin 47 may be provided to prevent the rotation of the threaded rod during pull back of the sheath to release the stent 11. The rod 40 may be joined to a pull wire 45, for example, by brazing. The pull wire 45 may in turn be joined to the sheath 20 by any suitable jointing means. For example, the sheath 20 may have it's diameter reduced by way of a constraining shrink tube. This ma y be shrunk onto either the pull wire 45 or alternately onto an adhesive layer on the wire 45. Alternatively, a ring bonded to the sheath 20 may be attached to the pull wire 45 by welding, brazing or adhesive jointing.

It will be appreciated that the linear actuation mechanism may be attached to the sheath 20 at any point along its length. For example, the attachment may be distal to the guidewire entrance lumen, at or near the lumen or at or close to the proximal end.

It will also be appreciated that while a slot is shown as a preferred embodiment, any configuration of sheath that is not continuous in it's circumference could be used to achieve the end objective of having a method of attachment to the stent covering sheath. For example, the constriction means may be in the form of a curved wrap-around body, for example in the form of a helix or part thereof.

It will further be appreciated that the stent may be of any suitable size or shape and may be of any desired material of construction.

The invention is not limited to the embodiments hereinbefore described which may be varied in construction and detail.

What is claimed is:

1. A rapid exchange stent delivery catheter for delivery and deployment of a stent comprising:

an elongate catheter body;

a self-expanding stent overlying said catheter body at a distal end thereof;

a sheath overlying said stent to constrict the stent during delivery;

the catheter body having a guidewire lumen with a guidewire exit at a distal end of the catheter body and a guidewire entrance proximal of the stent;

a guidewire extending through the lumen between the guidewire entrance and the guidewire exit; and a stent deployment assembly that moves the sheath relative to the catheter body to release the stent, the stent deployment assembly comprises a threaded shaft having a discontinuous thread, and a thumbwheel which is rotated to move the shaft linearly;

the sheath comprises a sheath opening arranged to align with the guidewire entrance and accomodate the guidewire so that the guidewire entrance is not obstructed during movement of the sheath relative to the catheter body on deployment of the stent.

2. A delivery catheter as claimed in claim 1 wherein the sheath opening is configured to correspond with the operation of the stent deployment assembly.

3. A delivery catheter as claimed in claim 1 wherein the sheath opening has a length which is greater than or equal to the length of the stent to be deployed.

4. A delivery catheter as claimed in claim 3 wherein the sheath opening comprises an elongate slot.

5. A delivery catheter as claimed in claim 1 further comprising an anti-rotation device to control rotation of the threaded shaft.

6. A delivery catheter as claimed in claim 1 wherein the thread is a multistart thread.

7. A delivery catheter as claimed in claim 6, wherein the thread is a four start thread.

8. A delivery catheter as claimed in claim 1 wherein the sheath opening is a helical slot such that a combined linear and rotational motion of the sheath maintains the opening for the guidewire.

9. A delivery catheter as claimed in claim 1 wherein the stent deployment assembly is attached to the sheath.

10. A delivery catheter as claimed in claim 9 wherein the stent deployment assembly comprises a pull wire attached directly or indirectly to the sheath.

11. A delivery catheter as claimed in claim 1 wherein the sheath opening is an elongate slot.

* * * * *